(12) United States Patent
Elokdah et al.

(10) Patent No.: US 7,135,492 B2
(45) Date of Patent: Nov. 14, 2006

(54) 1,3-DISUBSTITUTED-2-THIOXO-IMIDAZOLIDINE-4,5-DIONE DERIVATIVES USEFUL IN THE TREATMENT OF ATHEROSCLEROSIS

(75) Inventors: Hassan M. Elokdah, Yardley, PA (US); Theodore S. Sulkowski, Wayne, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/282,511

(22) Filed: Oct. 29, 2002

(65) Prior Publication Data

US 2003/0119889 A1 Jun. 26, 2003

Related U.S. Application Data

(60) Provisional application No. 60/341,046, filed on Oct. 30, 2001.

(51) Int. Cl.
*A61K 31/415* (2006.01)
*C07D 233/40* (2006.01)

(52) U.S. Cl. .................................. 514/390; 548/317.5
(58) Field of Classification Search ............. 548/317.5; 514/390
See application file for complete search history.

(56) References Cited

U.S. PATENT DOCUMENTS

| | | | |
|---|---|---|---|
| 3,461,133 A | 8/1969 | Stoffel | |
| 4,084,001 A | 4/1978 | Durant et al. | |
| 4,152,453 A | 5/1979 | Durant et al. | |
| 5,312,919 A | 5/1994 | Gulliya et al. | |
| 2003/0119890 A1 | 6/2003 | Batera et al. | |

FOREIGN PATENT DOCUMENTS

| | | |
|---|---|---|
| DE | 0154 819 | 4/1982 |
| DE | 219 483 A1 | 3/1985 |
| DE | 3540919 A1 | 5/1987 |
| EP | 0 718 290 B1 | 4/2002 |

OTHER PUBLICATIONS

Wanda Zankowska-Jasinska et al., Polish Journal of Pharmacology, "1,3-disubstituted 2-thioxo-4,5-imidazolidinediones and 2,4,5-imidazolidinetriones and their anticonvulsant activity" 1990, pp. 59-68.*
R. Beckert et al., Journal Fuer Praktische Chemie (1990) 331 (I), pp. 65-82; and Journal Fuer Praktische Chemie (1982) 324 (2) pp. 227-236.*
Barr, David P., et al. American Journal of Medicine, 11, 480-493 (1951).
Miller, J.G., et al., The Lancet, 1, 16-19 (1975).
Gordon, David J., et al., Circulation, 79(1), 8-15 (1989).
Stampfer, Meir J., et al., New England Journal of Medicine, 325(6), 373-381 (1991).
Baidmon, Juan Jose, et al., Laboratory Investigation, 60(3), 455-461 (1989).
Miller N.E., et al., British Medical Journal, 282, 1741-1744 (1981).
Picardo, Martino et al., Arteriosclerosis, 6(4), 434-441 (1986).
Glomset, John A., Journal of Lipid Research, 9, 155-167 (1968).
Glass, Christopher K., et al., The Journal of Biological Chemistry, 258(11), 7161-7167 (1983).
Mackinnon, Malcolm, et al., The Journal of Biological Chemistry, 261(6), 2548-2552 (1986).
Grow, Thomas E., et al., The Journal of Biological Chemistry, 8034-8041 (1978).
Lagocki, Peter A., et al., The Journal of Biological Chemistry, 255(8), (1980).
Kieft, Karen A., et al., Journal of Lipid Research, 32, 859-866 (1991).
Schaefer, Ernst J., et al., Journal of Lipid Research, 23, 1259-1273 (1982).
Gofman, John W., et al., Circulation, 34, 679-697 (1966).
Aguilar-Bryan et al., "Toward Understanding the Assembly and Structure of $K_{ATP}$ Channels", *Physiological Reviews*, 78:227-245 (1998).
Atwal, "Modulation of Potassium Channels by Organic Molecules", *Medicinal Research Reviews*, 12(6):569-591 (1992).
Beckert et al., "Reaction of oxalic amidines with carbonic acid derived heterocumulenes to imidazolidine derivatives", *Journal fuer Praktische Chemie*, 332(1):65-82 (1990) (Abstract only CAPLUS Accession No. 1990:497511; Document No. 113:97511).

(Continued)

*Primary Examiner*—Johann Richter
*Assistant Examiner*—Ebenezer Sackey
(74) *Attorney, Agent, or Firm*—Fish & Richardson P.C.

(57) ABSTRACT

Antiatherosclerotic compounds of Formula I are provided:

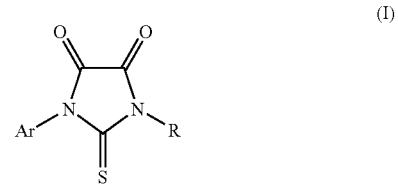

(I)

wherein:
R is lower alkyl, alkenyl, alkynyl, or —O—$(CH_2)_n$—COOR';
R' is lower alkyl;
n is an integer of 1–3;
Ar is phenyl, or phenyl substituted with one or more of halogen, lower alkyl, alkenyl, alkynyl, alkoxy, perfluoroalkyl, perfluoroalkoxy, or alkylthio; and pharmaceutically acceptable salts thereof.

30 Claims, No Drawings

OTHER PUBLICATIONS

Bonev et al., "ATP-sensitive potassium channels in smooth muscle cells from guinea pig urinary bladder", *Am. J. Physiol.*. 264:C1190-C1200 (1993).

Evans et al., "Potassium Channel Activators: Pharmacological Methods, Models, and Structure-Activity Relationships", *Progress in Medicinal Chemistry*, 31:411-447 (1994).

Fujii et al., "Potassium channel blockers and the effects of cromakalim on the smooth muscle of the guinea-pig bladder", *Br. J. Pharmacol.*, 99:779-785 (1990).

Garcia et al., "Pharmacology of Potassium Channels", *Advances in Pharmacology*, 39:425-471 (1997).

Gopalakrishnan et al., "ATP-Sensitive $K^+$ Channels: Pharmacologic Properties, Regulation and Therapeutic Potential", *Drug Development Research*, 28:95-127 (1993).

Grant et al., "Effect of $K^+$ Channel Blockers and Cromakalim (BRL 34915) on the Mechanical Activity of Guinea Pig Detrusor Smooth Muscle", *J. Pharmacol. Exp. Thera.*, 259(3):1158-1164 (1991).

Lawson, "Potassium Channel Activation: A Potential Therapeutic Approach?", *Pharmacol. Ther.*, 70:39-63. (1996).

Malmgren et al., "Effects of Cromakalim (BRL 34915) and Pinacidil on Normal and Hypertrophied Rat Detrusor in Vitro", *The Journal of Urology*, 143:828-834 (1990).

Malmgren et al., "Effects of Pinacidil and Cromakalim (BRL 34915) on Bladder Function in Rats with Detrusor Instability", *The Journal of Urology*, 142:1134-1138 (1989).

McDonough et al., "Overview of the Relationship Between Structure and Function in Ion Channels", *Drug Development Research*, 33:190-202 (1994).

Zankowska-Jasinska et al., "1,3-Disubstituted 2-thioxo-4, 5-imidazolidinediones and 2,4,5-imidazolidinetriones and their anticonvulsant activity", *Polish Journal of Pharmacology and Pharmacy*, 42(1):59-68 (1990) (Abstract only CAPLUS Accession No. 1991:75036; Document No. 1144:75036).

* cited by examiner

1,3-DISUBSTITUTED-2-THIOXO-IMIDAZOLIDINE-4,5-DIONE DERIVATIVES USEFUL IN THE TREATMENT OF ATHEROSCLEROSIS

This application claims priority from copending provisional application Ser. No. 60/341,046, filed Oct. 30, 2001, the entire disclosure of which is hereby incorporated by reference.

FIELD OF THE INVENTION

The present invention is directed to 1,3-disubstituted-2-thioxo-imidazolidine-4,5-dione derivatives that increase HDL concentration and are useful in the treatment of atherosclerotic conditions.

BACKGROUND OF THE INVENTION

Studies have demonstrated that both the risk of coronary heart disease (CHD) in humans and the severity of experimental atherosclerosis in animals are inversely correlated with serum high density lipoprotein cholesterol (HDL-C) concentrations (see, eg, Russ et al, *Am. J. Med.*, 11 (1951) 480–493; Gofman et al, *Circulation*, 34 (1966) 679–697; Miller and Miller, *Lancet*, 1 (1975) 16–19; Gordon et al, *Circulation*, 79 (1989)8–15; Stampfer et al, *N. Engl. J. Med.*, 325 (1991) 373–381; and Badimon et al, *Lab. Invest.*, 60 (1989) 455–461). Atherosclerosis is the process of the accumulation of cholesterol within the arterial wall which results in the occlusion or stenosis of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (see, eg, Miller et al, *Br. Med. J.*, 282 (1981) 1741–1744).

There are several mechanisms by which HDL may protect against the progression of atherosclerosis. Studies in vitro have shown that HDL is capable of removing cholesterol from cells (see, e.g., Picardo et al, *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (see, e.g., Glomset, *J. Lipid Res.*, 9 (1968) 155–167). This has been supported by experiments showing efficient transfer of cholesterol from HDL to the liver (see, eg, Glass et al., *J. Biol. Chem.*, 258 (1983) 7161–7167; MacKinnon et al, *J. Biol. Chem.*, 261 (1986) 2548–2552). In addition, HDL may serve as a reservoir in the circulation for apoproteins necessary for the rapid metabolism of triglyceride-rich lipoproteins (see, eg, Grow and Fried, *J. Biol. Chem.*, 253 (1978) 1834–1841; Lagocki and Scanu, *J. Biol. Chem.*, 255 (1980) 3701–3706; and Schaefer et al, *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

European Patent No. 718290-A1 claims carboxyalkyl heterocyclic derivatives as aldose reductase inhibitors useful in treating diabetic complications. Among compounds claimed are 4,5-dioxo-1-thioxoimidazolidines of the following formula:

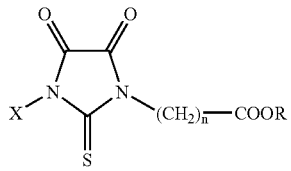

wherein:

R is hydrogen or lower alkyl of 1–3 carbon atoms;

n is an integer of 1–3; and

X is benzyl, benzothiazolylmethyl, or naphthyl methyl

U.S. Pat. No. 5,312,919 claims the preparation and use of merodantoin (1) as anticancer and antiviral agents. The patent further discloses compounds of formula 2:

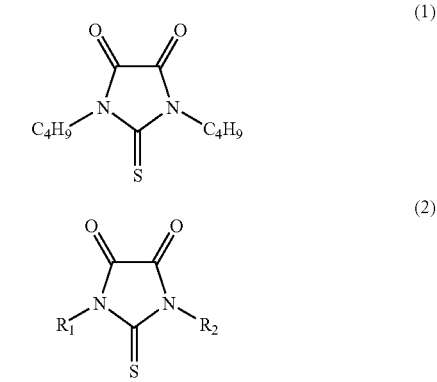

where $R_1$ and $R_2$ may be hydrogen, $C_1$–$C_6$ alkyl, or benzyl

U.S. Pat. Nos 4,084,001 and 4,152,453 claim the use of compounds of formula (1) as intermediates in the preparation of histamine blocking agents and as inhibitors of acid secretion (2).

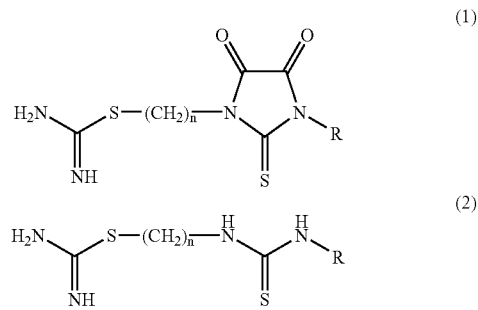

wherein:

R is alkyl and n is an integer of 1–6.

U.S. Pat. No. 3,461,133 discloses compounds of the following formula as herbicides:

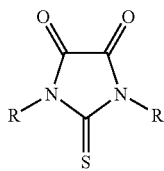

wherein:
R is an alkyl of 1–12 carbon atoms, alkenyl, or alkynyl.

German Patent DE 3540919 claims compounds of the following formula as herbicidal agents:

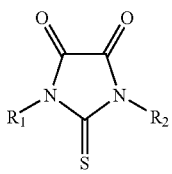

wherein:
$R_1$ is hydrogen, alkyl; and
$R_2$ is alkyl, phenyl, or phenylalkyl.

German Patent DD 154819 discloses methods for the preparation of compounds of formula (1) from 4,5-di-imino compounds (2)

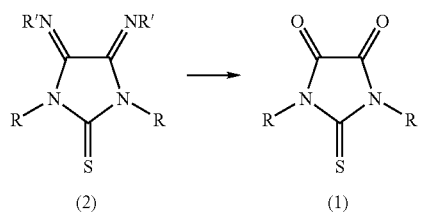

German Patent DD 219483 A1 discloses compounds of the following formula as antitubercular agents:

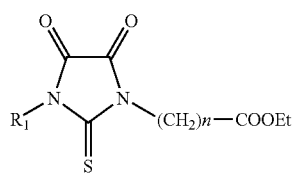

wherein:
R is aryl; and
n is an integer of 1–2.

SUMMARY OF THE INVENTION

The present invention is directed to a group of 1,3-disubstituted 2-thioxo-imidazolidine-4,5-dione derivatives of Formula I:

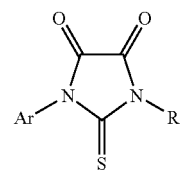

wherein: R is lower alkyl, alkenyl, alkynyl, or —O—$(CH_2)_n$—COOR';
R' is lower alkyl;
n is an integer of 1–3;
Ar is phenyl, or phenyl substituted with one or more of halogen, lower alkyl, alkenyl, alkynyl, alkoxy, perfluoroalkyl, perfluoroalkoxy, or alkylthio; and pharmaceutically acceptable salts thereof.

DETAILED DESCRIPTION OF THE INVENTION

Preferably, the compounds of the present invention are those of Formula I:

(I)

wherein:
R is lower alkyl, alkynyl, or —O—$(CH_2)_n$—COOR';
R' is lower alkyl;
n is 1–3;
Ar is phenyl substituted with halogen, lower alkyl, or alkylthio; and pharmaceutically acceptable salts thereof.

As used herein, the term "lower alkyl" meant to include both straight and branched carbon chains containing 1–10 atoms. The term "halogen" is meant to include fluorine, chlorine, bromine and iodine.

The pharmaceutically acceptable salts of the present compounds include derived from organic and inorganic acids much as acetic, citric, tartaric, succinic, fumaric, maleic, malonic, mandelic, malic, hydrochloric, hydrobromic, phosphoric, nitric, sulfuric, methanesulfonic, toluenesulfonic, and similarly human acceptable acids.

The most preferred compounds of this invention are:
Ethyl 2-{[3-(5-chloro-2-methylphenyl)-4,5-dioxo-2-thioxo-1-imidazolidinyl]oxy}acetate;
1-(4-Chloro-2-methylphenyl)-3-ethyl-2-thioxo-4,5-imidazolidinedione;
Ethyl 2-{[3-(5-chloro-2-methylphenyl)-4,5-dioxo-2-thioxo-1-imidazolidinyl]oxy}acetate;
1-(5-Chloro-2-methylphenyl)-3-methyl-2-thioxo-4,5-imidazolidinedione;
1-(2,6-Dimethylphenyl)-3-ethyl-2-thioxo-4,5-imidazolidinedione;
1-(5-Chloro-2-methylphenyl)-3-(2-propynyl)-2-thioxo-4,5-imidazolidinedione;

1-Ethyl-3-(5-fluoro-2-methylphenyl)-2-thioxo-4,5-imidazo-lidinedione; and 1-(2,6-Dimethylphenyl)-3-methyl-2-thioxo-4,5-imidazo-lidinedione.

The compounds of the invention can be prepared according to following reaction scheme I or a modification thereof using readily available starting materials, reagents and conventional synthetic procedures. It is also possible to make use of variants of these process steps, which in themselves are known to and well within the preparatory skill of the medicinal chemist. In the following reaction scheme R is alkyl, $R_1$ is alkyl, alkenyl, or alkynyl, $R_2$ and $R_3$ are independently hydrogen, halogen, alkyl, perfluoroalkyl, alkoxy, perfluoroalkoxy, alkenyl, alkynyl, alkylthio.

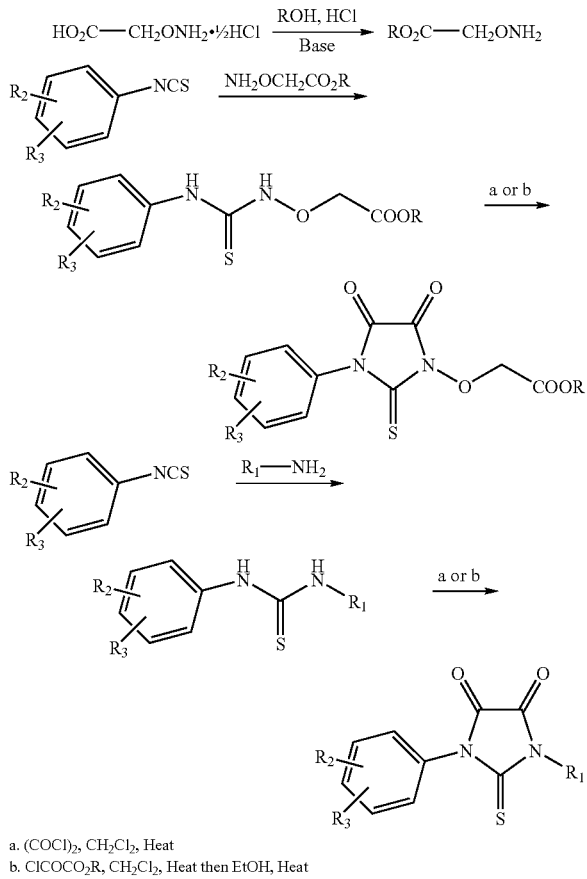

a. $(COCl)_2$, $CH_2Cl_2$, Heat
b. $ClCOCO_2R$, $CH_2Cl_2$, Heat then EtOH, Heat Carboxymethoxylamine hemihydrochloride was esterified with the appropriate alcohol saturated with hydrogen chloride. The reaction was carried out at ambient temperature for 24 hours. The solvent was evaporated and the residue was treated with a base such as sodium carbonate and extracted with a solvent such as ethyl acetate to give alkyl aminoxy acetate (2). Reaction of aryl isothiocyantes with either a primary amines or with the aminoxy acetate (2), in a solvent such as water, ether or methylene chloride for a period of 1 to 4 hours followed by evaporation of the solvent afforded either the N-alkyl thiourea or the N-alkyloxythiourea (3). Reaction of 3 with ethyl chlorooxoacetate at ambient temperature or under reflux condition for 1 to 18 hours in a solvent such as methylene chloride afforded the thioparabanate (4). Alternatively, the thioparabanate (4) can be obtained by reaction of 3 with oxalyl chloride by refluxing for 1 to 2 hours in a solvent such as methylene chloride. In this process, it was necessary to evaporate the reaction mixture to dryness, add ethanol and reflux for 1 to 2 hours.

This invention also provides pharmaceutical compositions comprising the compounds of the invention either alone or in combination with appropriate excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed in the treatment of such conditions depends upon several factors including the host, whether the compound is being used in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to increase blood serum HDL levels was established by the following standard experimental procedure for determination of HDL cholesterol:

Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances are 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contained 300 U/l cholesterol oxidase, 100 U/l cholesterol esterase, 1000 U/l horseradish peroxidase, 0.3 mmoles/l 4-aminoantipyrine and 30.0 mmoles/l p-hydroxybenzenesulfonate in a pH 6.5 buffer. In the reaction, cholesterol was oxidized to produce hydrogen peroxide which is used to form a quinoneimine dye. The concentration of dye formed was measured spectrophotometrically by absorbance at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., *J. Lipid Res.,* 32 (1991) 859–866. 25 ul of serum was injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample was mixed on line with Boehringer-Mannheim cholesterol reagent pumped at 0.2 ml/min. The combined eluents were mixed and incubated on line through a knitted coil (Applied Biosciences) maintained at a temperature of 45 C. The eluent was monitored by measuring absorbance at 490 nm and gave a continuous absorbance signal proportional to the cholesterol concentration. The relative concentration of each lipoprotein class was calculated as the percent of total absorbance. HDL cholesterol concentration, in serum, was calculated as the percent of total cholesterol as determined by FPLC multiplied by the total serum cholesterol concentration.

Test compounds were administered at a dose of 100 mg/kg. Each test substance is administered to a group of six rats. The duration of treatment was eight days. The compounds of the present invention increased HDL cholesterol concentrations as summarized in Table I:

TABLE 1

| Compound of Example | HDL Cholesterol Level Increase (%) |
|---|---|
| 1 | 242 |
| 2 | 196 |
| 3 | 19 |
| 4 | 203 |
| 5 | 186 |
| 6 | 227 |
| 7 | 199 |
| 8 | 103 |
| 9 | 114 |
| 10 | 36 |

The following examples are presented to illustrate the production of representative compounds useful in the methods of this invention, rather than as limit to the scope of the invention:

EXAMPLE 1

Step 1

Ethyl 2-(aminooxy) acetate 2-(Aminooxy) acetic acid hemihydrochloride (500 g) was suspended in ethanol (2000 mL). The mixture was saturated with hydrogen chloride and allowed to stand at room temperature for 24 hours. The mixture was then concentrated to the precipitation point. The solid was collected by filtration, washed with ether and dried to give ethyl 2-(aminooxy) acetate hydrochloride as a white solid (547 g), m.p. 115–117° C. Mass spectrum (EI, M.$^+$) m/z 119. $^1$H-NMR (DMSO-d$_6$; 300 MHz): δ 11.08 (br s, 3H), 4.74 (s, 2H), 4.16 (q, 2H), and 1.21 ppm (t, 3H).

Anal. for $C_4H_9NO_3$. HCl: Calcd: C, 30.88; H, 6.48; N, 9.00. Found: C, 30.55; H, 6.41; N, 9.16.

Ethyl 2-(aminooxy) acetate hydrochloride (24 g) was dissolved in water (100 mL). The solution was saturated with sodium bicarbonate and extracted with ethyl acetate (2×200 mL). The organic extract was washed with brine (100 mL), and dried over anhydrous magnesium sulfate. Evaporation of the solvent afforded ethyl 2-(aminoxy) acetate (15.8 g) as an oil. $^1$H-NMR (DMSO-d$_6$; 300 MHz): δ 6.28 (s, 2H), 4.12 (s, 2H), 4.10 (q, 2H), and 1.20 ppm (t, 3H).

Step 2

Ethyl 2-({[(5-chloro-2-methylanilino)carbothioyl]amino}oxy)acetate

5-Chloro2-methylphenyl isothiocyanate (18.3 g; 0.1 mol) was added dropwise to the solution of ethyl 2-(aminooxy)

acetate (11.9 g; 0.1 mol) in ether (30 mL). The mixture was stirred for 1 hour at ambient temperature. The solvent was evaporated. The residual solid was slurried in fresh ether then filtered. The solid was dried to give (25 g) of ethyl 2-({[(5-chloro-2-methylanilino) carbothioyl]amino}oxy)acetate, m.p. 117–119° C. Mass spectrum; FAB (M+H)$^+$ m/z 303. $^1$H-NMR (DMSO-d$_6$; 300 MHz): δ 11.08 (s, 1H), 9.85 (s, 1H), 7.37 (s, 1H), 7.26 (m, 2H), 4.53 (s, 2H), 4.17 (q, 2H), 2.18 (s, 3H), and 1.22 ppm (t, 3H).

Anal. for C$_{12}$H$_{15}$ClN$_2$O$_3$S: Calcd: C, 47.60; H, 4.99; N, 9.25. Found: C, 47.52; H, 4.94; N, 9.29.

Step 3

Ethyl 2-{[3-(5-chloro-2-methylphenyl)-4,5-dioxo-2-thioxo-1-imidazolidinyl]oxy}acetate Ethyl chlorooxoacetate (11.1 mL; 0.1 mol) was added dropwise to the solution of ethyl 2-({[(5-chloro-2-methylanilino) carbothioyl]amino}oxy)acetate (15.1 g; 0.05 mol) in methylene chloride (200 mL). The mixture was heated at reflux for 1 hour then evaporated to dryness. The residue was stirred in ether for 15 minutes and the solids were filtered. The solids were washed with fresh ether and dried to give 13.1 g of ethyl 2-{[3-(5-chloro-2-methylphenyl)-4,5-dioxo-2-thioxo-1-imidazolidinyl]oxy}acetate as a solid, m.p. 157–159° C. Mass spectrum; FAB (M+H)$^+$ m/z 357. $^1$H-NMR (DMSO-d$_6$; 300 MHz): δ 7.50 (d, 1H), 7.42 (m, 2H), 4.90 (q, 2H), 4.20 (q, 2H), 2.17 (s, 3H), and 1.24 ppm (t, 3H).

Anal. for C$_{14}$H$_{13}$Cl N$_2$O$_5$S: Calcd: C, 47.13; H, 3.67; N, 7.85. Found: C, 46.91; H, 3.52; N, 7.84.

EXAMPLE 2

Ethyl 2-({3-[2-(methylsulfanyl)phenyl]-4,5-dioxo-2-thioxo-1-imidazolidinyl}oxy)acetate 1-Isothiocyanato-2-(methylsulfanyl)benzene (9.05 g; 0.05 mol) was added dropwise to the solution of ethyl 2-(aminooxy) acetate (5.95 g; 0.05 mol) in ether (20 mL). The mixture was stirred for 1 hour at ambient temperature. The solvent was evaporated. The residue was dissolved in ether (400 mL) and washed with 2NHCl (2×200 mL) then with water (200 mL). The organic phase was dried over anhydrous magnesium sulfate and evaporated to dryness. The residual oil solidifies upon standing to give ethyl 2-[({[2-(methylsulfanyl)anilino]carbothioyl}amino) oxy] acetate (15.1 g).

Oxalyl chloride (10.2 g; 0.08 mol) was added dropwise to the solution of ethyl 2-[({[2-(methylsulfanyl)anilino] carbothioyl}amino)oxy]acetate (12 g, 0.04 mol) in methylene chloride (100 mL). The mixture was heated at reflux for 1 hour then evaporated to dryness. The residue was treated with ethanol (100 mL) and the mixture was heated at reflux for 1 hour. The mixture was evaporated to dryness. The residue was chromatographed on silica gel (20%ethyl acetate in hexane). Ethyl 2-({3-[2-(methylsulfanyl)phenyl]-4,5-dioxo-2-thioxo-1-imidazolidinyl}oxy)acetate (4.7 g) was obtained as a solid, m.p. 112–114° C. Mass spectrum; (EI, M.$^+$) m/z 354. $^1$H-NMR (DMSO-d$_6$; 300 MHz): δ 7.56–7.46 (m, 2H), 7.34 (m, 2H), 4.94 (q, 2H), 4.19 (q, 2H), 2.43 (s, 3H), and 1.23 ppm (t, 3H).

Anal. for C$_{14}$H$_{14}$N$_2$O$_5$S$_2$: Calcd: C, 47.45; H, 3.98; N, 7.91. Found: C, 46.34; H, 3.87; N, 7.87.

EXAMPLE 3

1-(5-Chloro-2-methylphenyl)-3-ethyl-2-thioxo-4,5-imidazolidinedione

5-Chloro-2-methylphenyl isothiocyanate (18.3 g; 0.1 mol) was added dropwise to aqueous ethylamine (200 mL of 70% solution). The mixture was stirred for 18 hour at ambient temperature. Excess ethylamine was removed under a stream of nitrogen. The residue was diluted with water. The solids were collected by filtration, washed with water and dried to give N-(5-chloro-2-methylphenyl)-N'-ethylthiourea (18.9 g). A sample crystallized from ethyl acetate afforded a solid, m.p. 120–122° C. Mass spectrum;; FAB (M+H)$^+$ m/z 228. $^1$H-NMR (DMSO-d$_6$; 300 MHz): δ 9.01 (br s, 1H), 7.67 (br s, 1H), 7.35 (br s, 1H), 7.25–7.16 (m, 2H), 3.44 (m, 2H), 2.13 (s, 3H), and 1.08 ppm (t, 3H).

Anal. for C$_{10}$H$_{13}$ClN$_2$S: Calcd: C, 52.51; H, 5.73; N, 12.25. Found: C, 52.54; H, 5.76; N, 12.26.

Ethyl chlorooxoacetate (12.3 g; 0.09 mol) was added dropwise to the solution N-(5-chloro-2-methylphenyl)-N'-ethylthiourea (13.7 g; 0.06 mol) in chloroform (300 mL). The mixture was heated at reflux for 3 hour then evaporated to dryness. The residue was dissolved in ethyl acetate (400 mL) and washed with saturated sodium bicarbonate solution (300 mL), then with water (300 mL). ). The organic phase was dried over anhydrous magnesium sulfate and evaporated to dryness. The residual solid was slurried in ether and filtered. The solid was washed with ether and air dried to give 1-(5-Chloro-2-methylphenyl)-3-ethyl-2-thioxo-4,5-imidazolidinedione (14.1 g), m.p. 173–174° C. Mass spectrum; (EI, M.$^+$) m/z 382/384. $^1$ H-NMR (DMSO-d$_6$; 300 MHz): δ 7.49–7.40 (m, 3H), 3.92 (m, 2H), 2.15 (s, 3H), and 1.23 ppm (t, 3H).

Anal. for C$_{12}$H$_{11}$ClN$_2$O$_2$S: Calcd: C, 50.98; H, 3.92; N, 9.91. Found: C, 51.03; H, 3.61; N, 9.79.

EXAMPLE 4

1-Ethyl-3-(5-fluoro-2-methylphenyl)-2-thioxo-4,5-imidazolidinedione

5-Fluoro-2-methylphenyl isothiocyanate (16.7 g; 0.1 mol) was added dropwise to aqueous ethylamine (120 mL of 70% solution). The mixture was stirred for 2 hour at ambient temperature. Excess ethylamine was removed under a stream of nitrogen. The residue was diluted with water. The solids were collected by filtration, washed with water and dried. The solid was dissolved in ether and washed with water. The organic phase was dried over anhydrous magnesium sulfate then evaporated to dryness to give N-(5-fluoro-2-methylphenyl)-N'-ethylthiourea (18.5 g), m.p. 93–95° C. Mass spectrum; (EI, M.$^+$) m/z 212. $^1$H-NMR (DMSO-d$_6$; 300 MHz): δ 9.01 (br s, 1H), 7.66 (br s, 1H), 7.25–7.18 (m, 2H), 6.96 (m, 1H), 3.45 (m, 2H), 2.13 (s, 3H), and 1.09 ppm (t, 3H).

Anal. for C$_{10}$H$_{13}$FN$_2$S: Calcd: C, 56.58; H, 6.17; N, 13.20. Found: C, 56.53; H, 6.04; N, 13.17.

Oxalyl chloride (12.7 g; 0.1 mol) was added dropwise to the solution N-(5-chloro-2-methylphenyl)-N'-ethylthiourea (10.6 g; 0.05 mol) in methylene chloride (100 mL). The mixture was heated at reflux for 2 hour then evaporated to dryness. The residue was dissolved in ethanol (100 mL) and heated at reflux for 1 hour. The mixture was cooled to ambient temperature. The precipitated solid was collected by filtration and dried to give 1-ethyl-3-(5-fluoro-2-methylphenyl)-2-thioxo-4,5-imidazolidinedione (6.4 g), m.p.

152–153° C. Mass spectrum; (EI, M.$^+$) m/z 266. $^1$H-NMR (DMSO-d$_6$; 300 MHz): δ 7.42 (m, 1H), 7.31–7.26 (m, 1H), 7.21–7.18 (m, 1H), 3.91 (m, 2H), 2.13 (s, 3H), and 1.23 ppm (t, 3H).

Anal. for C$_{12}$H$_{11}$FN$_2$O$_2$S: Calcd: C, 54.13; H, 4.16; N, 10.52. Found: C, 53.76; H, 3.99; N, 10.46.

EXAMPLE 5

1-(5-Chloro-2-methylphenyl)-3-methyl-2-thioxo-4,5-imidazolidinedione

5-Chloro-2-methylphenyl isothiocyanate (36.6 g; 0.2 mol) was added to the solution of methylamine hydrochloride (26.8 g; 0.4 mol) in chloroform (300 mL). Triethylamine (65 mL; 0.47 mol) was added dropwise while stirring at ambient temperature. The mixture was stirred for 18 hours. The solvent was evaporated. The residue was treated with ethyl acetate (800 mL) and water (400 mL). The organic phase was separated, washed with water (2×300 mL), dried over magnesium sulfate and evaporated to dryness to give 41.6 g of N-(5-chloro-2-methylphenyl)-N'-methylthiourea, m.p. 139–140° C.

Ethyl chlorooxoacetate (16.3 g; 0.128 mol) was added dropwise to the solution N-(5-chloro-2-methylphenyl)-N'-methylthiourea (10.7 g; 0.05 mol) in chloroform (200 mL). The mixture was heated at reflux for 4 hours then evaporated to dryness. The residue was treated with ether (200 mL). The precipitated solid was collected by filtration and dried to give 9.7 g of 1-(5-chloro-2-methylphenyl)-3-methyl-2-thioxo-4,5-imidazolidinedione, m.p. 171–173° C. Mass spectrum; (EI, M.$^+$) m/z268/270. $^1$H-NMR (DMSO-d$_6$; 300 MHz): δ 7.50–7.47 (m, 1H), 7.42–7.40 (m, 2H), 3.31 (s, 3H), and 2.15 ppm (s, 3H).

Anal. for C$_{11}$H$_9$ClN$_2$O$_2$S: Calcd: C, 49.17; H, 3.38; N, 10.42. Found: C, 49.08; H, 3.19; N, 10.40.

EXAMPLE 6

1-(2,6-Dimethylphenyl)-3-methyl-2-thioxo-4,5-imidazolidinedione 2,6-Dimethylphenyl isothiocyanate (7.65 g; 0.047 mol) was added dropwise to 100 mL of 40% aqueous methylamine solution. The mixture was stirred for 1 hour at ambient temperature. The mixture was extracted with ethyl acetate (2×300 mL) solvent was evaporated. The residue was treated with ethyl acetate (800 mL) and water (400 mL). The organic extracts were combined, washed with water, dried over magnesium sulfate and evaporated to dryness. The residual oil solidified upon standing. The crystalline mass was crushed and stirred in hexane. The solid was collected by filtration and dried to 7.74 g of N-(2,6-dimethylphenyl)-N'-methylthiourea, m.p. 95–97° C. Mass spectrum; (EI, M.$^+$) m/z 194. $^1$H-NMR (DMSO-d$_6$; 300 MHz): δ 9.05–8.84 (br s, 1H), 7.08 (br s, 3H), 6.8 (br s,1H), 2.85 (s, 3H), and 2.12 ppm (s, 6H).

Anal. for C$_{10}$H$_{14}$N$_2$S: Calcd: C, 61.82; H, 7.26; N, 14.42. Found: C, 61.71; H, 7.26; N, 14.40.

Oxalyl chloride (8.4 g; 0.066 mol) was added dropwise to the stirring solution of N-(2,6-dimethyl phenyl)-N'-methylthiourea (6.4 g; 0.033 mol) in methylene chloride (100 mL). The mixture was heated at reflux for 2 hours then evaporated to dryness. Ethanol (100 mL) was added and the mixture was heated at reflux for 1 hour. The solvent was concentrated. The precipitated solid was collected by filtration and dried to give 5.4 g of 1-(2,6-Dimethylphenyl)-3-methyl-2-thioxo-4,5-imidazolidinedione, m.p. 144–146° C. Mass spectrum; (EI, M.$^+$) m/z248. $^1$H-NMR (DMSO-d$_6$; 300 MHz): δ 7.30 (t, 1H), 7.18 (d, 2H), 3.33 (s, 3H), and 2.08 ppm (s, 6H).

Anal. for C$_{12}$H$_{12}$N$_2$O$_2$S: Calcd: C, 58.05; H, 4.87; N, 11.28. Found: C, 58.05; H, 4.75; N, 11.24.

EXAMPLE 7

1-Ethyl-3-(4-fluorophenyl)-2-thioxo-4,5-imidazolidinedione

4-Fluorophenyl isothiocyanate (15.3 g; 0.1 mol) was added dropwise to 200 mL of 70% aqueous ethylamine solution. The mixture was stirred for 2 hours at ambient temperature. Excess ethylamine was evaporated under a stream of nitrogen. The mixture was diluted with water (300 mL). The solid was collected by filtration and dried to 18.9 g of N-ethyl-N'-(4-fluorophenyl) thiourea.

Oxalyl chloride (12.7 g; 0.1 mol) was added dropwise to the stirring solution of N-ethyl-N'-(4-fluorophenyl) thiourea (16 g; 0.08 mol) in methylene chloride (200 mL). The mixture was heated at reflux for 1 hour then evaporated to dryness. Ethanol (200 mL) was added and the mixture was heated at reflux for 1 hour then evaporated to dryness. The residue was dissolved in ethyl acetate (500 mL) and washed with 2N hydrochloric acid (2×400 mL) then with water (400 mL). The organic phase was dried over anhydrous magnesium sulfate and evaporated to dryness. The residue was crystallized from ethyl acetate/hexane to give 19.1 g of 1-ethyl-3-(4-fluorophenyl)-2-thioxo-4,5-imidazolidinedione, m.p. 172–174° C. Mass spectrum; FAB (M+H)$^+$ m/z 253. $^1$H-NMR (DMSO-d$_6$; 300 MHz): δ 7.42–7.34 (m, 4H), 3.92 (q, 2H), and 1.22 ppm (t, 3H).

Anal. for C$_{11}$H$_9$FN$_2$O$_2$S: Calcd: C, 52.37; H, 3.60; N, 11.10. Found: C, 52.15; H, 3.40; N, 11.15.

EXAMPLE 8

1-(4-Chloro-2-methylphenyl)-3-ethyl-2-thioxo-4,5-imidazolidinedione

4-Chloro-2-methylphenyl isothiocyanate (18.3 g; 0.1 mol) was added dropwise to 200 mL of 70% aqueous ethylamine solution. The mixture was stirred for 2 hours at ambient temperature. Excess ethylamine was evaporated under a stream of nitrogen. The mixture was diluted with water (300 mL). The solid was collected by filtration and dissolved in ethyl acetate (500 mL) then washed with water (300 mL). The organic phase was dried over anhydrous magnesium sulfate and evaporated to dryness. The residual oil solidified to give dried to 18.0 g of N-(4-chloro-2-methylphenyl)-N'-ethylthiourea.

Oxalyl chloride (10.5 g; 0.082 mol) was added dropwise to the stirring solution of N-(4-chloro-2-methylphenyl)-N'-ethylthiourea (17 g; 0.075 mol) in methylene chloride (200 mL). The mixture was heated at reflux for 1 hour then evaporated to dryness. Ethanol (100 mL) was added and the mixture was heated at reflux for 1 hour then evaporated to dryness. The residue was dissolved in ethyl acetate (500 mL) and washed with 2N hydrochloric acid (500 mL) then with water (300 mL). The organic phase was dried over anhydrous magnesium sulfate and evaporated to dryness. The residue was crystallized from ethyl acetate/hexane to give 13.2 g of 1-(4-chloro-2-methylphenyl)-3-ethyl-2-thioxo-4,5-imidazolidinedione, m.p. 161–162° C. Mass spectrum; FAB (M+H)$^+$ m/z 283. $^1$H-NMR (DMSO-d$_6$; 300 MHz): δ

7.49 (d, 1H), 7.39 (m,1H), 7.33 (d, 1H), 3.91 (m, 2H), 2.16 (s, 3H), and 1.23 ppm (t, 3H).

Anal. for $C_{12}H_{11}ClN_2O_2S$: Calcd: C, 50.98; H, 3.92; N, 9.91. Found: C, 50.67; H, 3.68; N, 9.83.

EXAMPLE 9

1-(5-Chloro-2-methylphenyl)-3-(2-propynyl)-2-thioxo-4,5-imidazolidinedione

5-Chloro-2-methylphenyl isothiocyanate (18.3 g; 0.1 mol) was added dropwise to the mixture of 2-propynylamine hydrochloride (9.2 g, 0.1 mol) and triethyl amine (20 mL) in methylene chloride (200 mL). The mixture was stirred for 18 hours at ambient temperature. The mixture was evaporated to dryness. The residue was stirred in water (200 mL) for 1 hour then filtered. The solid was dissolved in ethyl acetate (300 mL) and washed with 1N hydrochloric acid (2×200 mL) then with water (300 mL). The organic phase was dried over anhydrous magnesium sulfate and evaporated to dryness to give 16.8 g of N-(5-chloro-2-methylphenyl)-N'-(2-propynyl)thiourea.

Ethyl chlorooxoacetate (11.2 mL; 0.1 mol) was added dropwise while cooling in an ice bath to the stirring solution of N-(5-chloro-2-methylphenyl)-N'-(2-propynyl)thiourea (11.95 g; 0.05 mol) in methylene chloride (200 mL). The mixture was stirred for 18 hours at ambient temperature then evaporated to dryness. The residue was stirred in ether (200 mL) and the solids were collected by filtration and air dried to give 3.0 g 1-(5-chloro-2-methylphenyl)-3-(2-propynyl)-2-thioxo-4,5-imidazolidinedione, m.p. 162–164° C. Mass spectrum; (El, M.$^+$) m/z 292/294. $^1$H-NMR (DMSO-d$_6$; 300 MHz): δ 7.50–7.47 (m, 2H), 7.73 (d, 1H), 4.66 (q, 2H), 3.37 (t, 1H), and 2.15 ppm (s,3H).

Anal. for $C_{13}H_9ClN_2O_2S$: Calcd: C, 53.34; H, 3.10; N, 9.57. Found: C, 53.28; H, 2.95; N, 9.42.

EXAMPLE 10

1-(2,6-Dimethylphenyl)-3-ethyl-2-thioxo-4,5-imidazolidinedione 2,6-Dimethylphenyl isothiocyanate (16.3 g; 0.1 mol) was added dropwise to 110 mL of 70% aqueous ethylamine solution. The mixture was stirred for 1 hour at ambient temperature. Excess ethylamine was evaporated under a stream of nitrogen. The mixture was diluted with water (100 mL). The solid was collected by filtration and washed with water and dried to give 20.0 g of N-(2,6-dimethylphenyl)-N'-ethylthiourea.

Oxalyl chloride (7.62 g; 0.06 mol) was added dropwise to the stirring solution of N-(2,6-dimethylphenyl)-N'-ethylthiourea (10.4 g; 0.05 mol) in methylene chloride (200 mL). The mixture was heated at reflux for 1 hour then evaporated to dryness. Ethanol (100 mL) was added and the mixture was heated at reflux for 1 hour then evaporated to dryness. The residue was dissolved in ethyl acetate (300 mL) and washed with 2N hydrochloric acid (500 mL) then with water (300 mL). The organic phase was dried over anhydrous magnesium sulfate and evaporated to dryness. The residue was crystallized from ether/hexane to give 6.0 g of 1-(2,6-Dimethylphenyl)-3-ethyl-2-thioxo-4,5-imidazolidinedione, m.p. 103–105° C. Mass spectrum; FAB (M+H)$^+$ m/z 263. $^1$H-NMR (DMSO-d$_6$; 300 MHz): δ 7.31–7.27 (m, 1H), 7.18 (d, 2H), 3.94 (q, 2H), 2.08 (s, 6H), and 1.25 ppm (t, 3H).

Anal. for $C_{13}H_{14}N_2O_2S$: Calcd: C, 59.52; H, 5.38; N, 10.68. Found: C, 59.55; H, 5.30; N, 10.66.

The present invention may be embodied in other specific forms without departing from the spirit and essential attributes thereof and accordingly, reference should be made to the appended claims rather than to the foregoing specification as indicating the scope of the invention.

What is claimed is:

1. Antiatherosclerotic compounds of Formula I

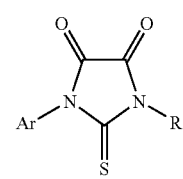

(1)

wherein:
R is lower alkyl, alkenyl, alkynyl, or —O—(CH$_2$)$_n$—COOR';
R' is lower alkyl;
n is an integer of 1–3;
Ar is phenyl substituted with one or more of halogen, lower alkyl, alkenyl, alkynyl, perfluoroalkyl, perfluoroalkoxy, or alkylthio; and pharmaceutically acceptable salts thereof.

2. The antiatherosclerotic compounds of claim 1 wherein:
R is lower alkyl, alkynyl, or —O—(CH$_2$)$_n$—COOR';
R' is lower alkyl;
n is an integer of 1–3; and
Ar is phenyl substituted with halogen, lower alkyl or alkylthio; and pharmaceutically acceptable salts thereof.

3. The compound of claim 1 which is ethyl 2-{[3-(5-chloro-2 methylphenyl)-4,5-dioxo-2-thioxo-1-imidazolidinyl]oxy}acetate.

4. The compound of claim 1 which is 1-(4-chloro-2-methylphenyl)-3-ethyl-2-thioxo-4,5-imidazolidinedione.

5. The compound of claim 1 which is 1-(5-chloro-2-methylphenyl)-3-methyl-2-thioxo-4,5-imidazolidinedione.

6. The compound of claim 1 which is 1-(2,6-dimethylphenyl)-3-methyl-2-thioxo-4,5-imidazolidinedione.

7. The compound of claim 1 which is 1-(5-chloro-2-methylphenyl)-3-(2-propynyl)-2-thioxo-4,5-imidazolidinedione.

8. The compound of claim 1 which is 1-ethyl-3-(5-fluoro-2-methylphenyl)-2-thioxo-4,5-imidazolidinedione.

9. The compound of claim 1 which is 1-(2,6-dimethylphenyl)-3-methyl-2-thioxo-4,5-imidazolidinedione.

10. A pharmaceutical composition comprising a pharmaceutically acceptable carrier and a compound of Formula I:

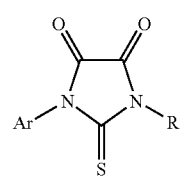

(I)

wherein:
R is lower alkyl, alkenyl, alkynyl, or —O—(CH$_2$)$_n$—COOR';
R' is lower alkyl;
n is an integer of 1–3;

Ar is phenyl substituted with one or more of halogen, lower alkyl, alkenyl, alkynyl, perfluoroalkyl, perfluoroalkoxy, or alkylthio; and pharmaceutically acceptable salts thereof.

11. A method for treating atherosclerosis in a mammal in need thereof, comprising administering to said mammal an anti-atherosclerotic effective amount of a compound of Formula I:

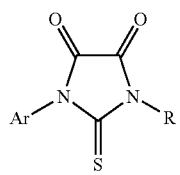
(1)

wherein:
R is alkenyl, alkynyl, or —O—(CH$_2$)$_n$—COOR';
R' is lower alkyl;
n is an integer of 1–3;
Ar is phenyl, or phenyl substituted with one or more of halogen, lower alkyl, alkenyl, alkynyl, alkoxy, perfluoroalkyl, perfluoroalkoxy, or alkylthio; and pharmaceutically acceptable salts thereof.

12. The compounds of claim 1, wherein R is straight chain lower alkyl, alkenyl, alkynyl, or —O—(CH$_2$)$_n$—COOR'.

13. The compounds of claim 1, wherein R is —CH$_3$, —CH$_2$CH$_3$, alkenyl, alkynyl, or —O—(CH$_2$)$_n$—COOR'.

14. The compounds of claim 1, wherein R is lower alkyl, alkynyl, or —O—(CH$_2$)$_n$—COOR'.

15. The compounds of claim 14, wherein R is straight chain lower alkyl, alkynyl, or —O—(CH$_2$)$_n$—COOR'.

16. The compounds of claim 14, wherein R is —CH$_3$, —CH$_2$CH$_3$, alkynyl, or —O—(CH$_2$)$_n$—COOR'.

17. The compounds of claim 14, wherein R is —CH$_3$, —CH$_2$CH$_3$, —CH$_2$C≡CH, or —O—CH$_2$—COOCH$_2$CH$_3$.

18. The compounds of claim 2 wherein R is straight chain lower alkyl, alkynyl, or —O—(CH$_2$)$_n$—COOR'.

19. The compounds of claim 2 wherein R is CH$_3$, CH$_2$CH$_3$, alkynyl, or —O—(CH$_2$)$_n$—COOR'.

20. The antiatherosclerotic compounds of claim 2 wherein R is —CH$_3$, —CH$_2$CH$_3$, —CH$_2$C≡CH, or —O—(CH$_2$)$_n$—COO CH$_2$CH$_3$.

21. A method for treating atherosclerosis in a mammal in need thereof, comprising administering to said mammal an anti-atherosclerotic effective amount of a compound of Formula I:

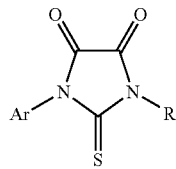
(1)

wherein:
R is lower alkyl, alkenyl, alkynyl, or —O—(CH$_2$)$_n$—COOR';
R' is lower alkyl;
n is an integer of 1–3;
Ar is phenyl, or phenyl substituted with one or more of halogen, lower alkyl, alkenyl, alkynyl, alkoxy, perfluoroalkyl, perfluoroalkoxy, or alkylthio; and pharmaceutically acceptable salts thereof.

22. A compound having Formula I

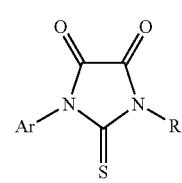
(1)

wherein:
R is lower alkyl, alkenyl, alkynyl, or —O—(CH$_2$)$_n$—COOR';
R' is lower alkyl;
n is an integer of 1–3;
Ar is phenyl substituted with one or more of halogen, lower alkyl, alkenyl, alkynyl, perfluoroalkyl, perfluoroalkoxy, or alkylthio; and pharmaceutically acceptable salts thereof.

23. The compound of claim 22, wherein:
R is lower alkyl, alkynyl, or —O—(CH$_2$)$_n$—COOR';
R' is lower alkyl;
n is an integer of 1–3; and
Ar is phenyl substituted with halogen, lower alkyl or alkylthio; and pharmaceutically acceptable salts thereof.

24. The compound of claim 22, which is ethyl 2-{[3-(5-chloro-2methylphenyl)-4,5-dioxo-2-thioxo-1-imidazolidinyl]oxy}acetate.

25. The compound of claim 22, which is 1-(4-chloro-2-methylphenyl)-3-ethyl-2-thioxo-4,5-imidazolidinedione.

26. The compound of claim 22, which is 1-(5-chloro-2-methylphenyl)-3-methyl-2-thioxo-4,5-imidazolidinedione.

27. The compound of claim 22, which is 1-(2,6-dimethylphenyl)-3-methyl-2-thioxo-4,5-imidazolidinedione.

28. The compound of claim 22, which is 1-(5-chloro-2-methylphenyl)-3-(2-propynyl)-2-thioxo-4,5-imidazolidinedione.

29. The compound of claim 22, which is 1-ethyl-3-(5-fluoro-2-methylphenyl)-2-thioxo-4,5-imidazolidinedione.

30. The compound of claim 22, which is 1-(2,6-dimethylphenyl)-3-methyl-2-thioxo-4,5-imidazolidinedione.

* * * * *